United States Patent [19]

Jimenez-Bayardo et al.

[11] Patent Number: 6,071,958

[45] Date of Patent: Jun. 6, 2000

[54] OPHTHALMIC CARRIER SOLUTION

[75] Inventors: Arturo Jimenez-Bayardo, Avenida Hidalgo No. 737, Colonia Centro, C.P., 44290, Guadalajara, Jalisco; Jose Ruben Tornero-Montaño, Jalisco; Gregorio Cuevas-Pacheco, Jalisco; Juan Manuel Diaz-Perez, Jalisco; Maria Elena Garcia-Armenta, Jalisco, all of Mexico

[73] Assignee: Arturo Jimenez-Bayardo, Jalisco, Mexico

[21] Appl. No.: 08/958,681

[22] Filed: Oct. 27, 1997

[30] Foreign Application Priority Data

Mar. 14, 1997 [MX] Mexico ..................................... 971946

[51] Int. Cl.[7] .................................................... A61K 31/24
[52] U.S. Cl. ........................... 514/535; 514/772; 514/912
[58] Field of Search ..................................... 514/535, 772, 514/912

[56] References Cited

PUBLICATIONS

Chemical Abstract 126:255499 (1995). Haraguchi et al.
Chemical Abstract 103:42640 (1983). Showa.
Chemical Abstract 128: 132459 (1996). Doi et al.

*Primary Examiner*—Zohreh Fay
*Attorney, Agent, or Firm*—Ladas & Parry

[57] ABSTRACT

This invention refers to a matter composition of the type used in the treatment of ophthalmic ailments and specifically refers to an ophthalmic carrier solution based on surface-active, emulsifying, antibacterial, antioxidant, etc. Agents which form a carrier that enwraps or masks an active ingredient such as sodium dyclophenac or other antibiotic agents such as tobracin, gentamicin or timolol sulfate, with the aim of avoiding the problems caused by the topical application of the mentioned active ingredients, such as pain, a burning sensation, irritation and other annoyances for the user.

9 Claims, 2 Drawing Sheets

OPHTHALMIC CARRIER SOLUTION

TECHNICAL FIELD OF THE INVENTION

This invention belongs to the field of matter compositions used for ophthalmic treatments, and specifically it deals with an aqueous solution with characteristics similar to the human pre-corneal lachrymal film, which prevents a user from feeling pain or a burning sensation due to the application of a topical ophthalmic medication, and which also increases the ocular penetration of the ophthalmic composition and its bio-availability.

BACKGROUND TO THE INVENTION

Medicines exist in the international ophthalmological pharmaceutical market which when applied topically cause a burning sensation and irritation of the eye.

Taking this situation as a basis, it was thought to use some type of compound with anti-inflammatory characteristics which could be used as an eyewash to treat eye irritations. It was found that a compound derived from acetic phenyl acid, called sodium dyclophenac i.e., sodium acetate of o-(2,6-dichlorophenyl)-amino-phenyl, whose preparation method is described in U.S. Pat. No. 3,558,690 belonging to Geigy, would meet expectations for a suitable ophthalmic application. However, the main disadvantage present in this compound, is the intense burning sensation and irritation it produces in the eyes of the user, which makes it unsuitable for use.

Despite the above disadvantage, taking into account the anti-inflammatory properties of sodium dyclophenac, the preparation of a suitable carrier was thought of which would allow the application of the mentioned compound but without the associated problems of a burning sensation and irritation and with this in mind, the final formulation of the carrier or ophthalmic carrier solution which is the motive of this invention was reached.

In virtue of the above, the object of this invention is to provide an ophthalmic carrier solution suitable for the topical application of ophthalmic solutions of several different types, among them, sodium dyclophenac or antibiotics such as tobramicin, gentamicin and timolol sulfate.

Another object of this invention is that of allowing a compound based on sodium dyclophenac to reach the human eye, which usually causes pain, a burning sensation, temporary irritation and weeping as undesirable effects of its topical application, but without the inherent problems of pain, the burning sensation and irritation.

Another additional objective of this invention is that of preparing a formulation which contains the active ingredient but which is effective for avoiding the mentioned undesirable effects.

DETAILED DESCRIPTION OF THE INVENTION

Figure 1:
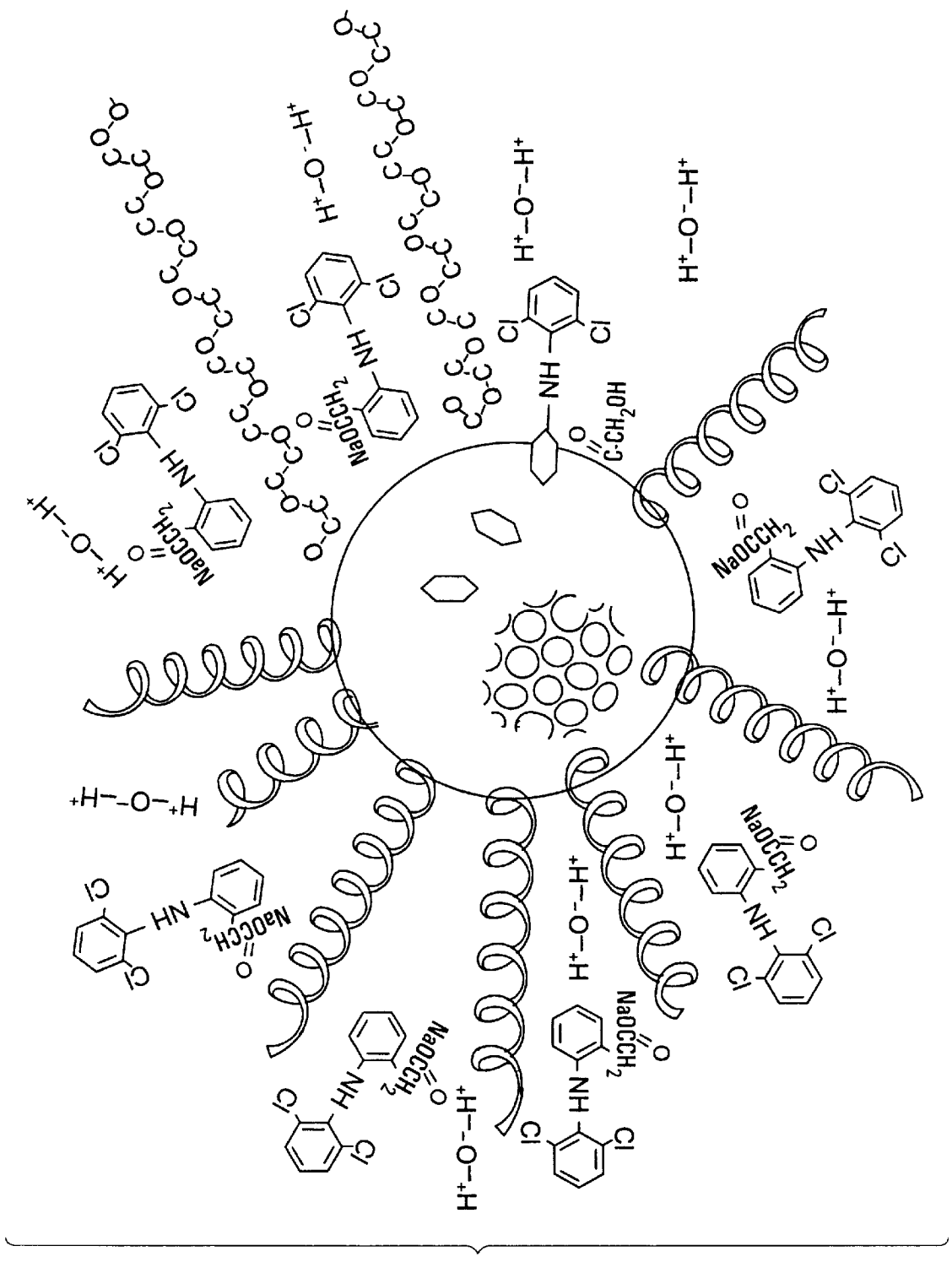
FIG. 1, is a diagram of the reaction which takes place between the components of the formula of this invention and the main active ingredient.

Considering the anatomy and histology of the eyeball, of the conjunctiva and the cornea and their abundant innervation by 6 of the 12 cranial pairs, it was thought to try to avoid and/or reduce the umbral of the painful stimulate and burning sensation principally due to the presence of solutions containing ocular topical application drugs and/or active ingredients.

Starting with the above, specialist ophthalmologists were consulted with the aim of seeing the structure of the eyeball with regards to its anatomy, physiology and biochemistry in order to understand the interaction of the developments, demonstrating the balance achieved with the interaction, carrying, penetration and action of the drug without the classic side effects present in this and other medicines. From the above it has been proved that the desired results have been obtained as the clinical tests performed demonstrate that the carrier solution of the invention does not have the classic undesirable effects.

With the desired objectives in mind, a bibliographic examination was made of ingredients, excipients, support molecules which contain an active ingredient (in this case Sodium dyclophenac). It was found that all the compounds are water based and some in an oily state. For our case, the following, based on this bibliographical examination and experience, was considered:

Starting from a surface-active molecule which has a molecular weight which varies between 1900 and 2100 and which has the characteristic of possessing two molecular fractions: one fraction a which is not polar and a fraction b which is polar. The first fraction has a molecular weight between 200 and 250 and the polar fraction b has a molecular weight between 1750 and 1850, the above based on the need to have a molecule of these characteristics in order to maintain its highly excited polar structure, also considering that it must maintain a pH close to neutrality or neutral (6.8–7.2).

The molecule which has these characteristics is polyoxyl stearate 40 whose formula and stoichiometric position allows the active ingredient, in this case sodium dyclophenac, to be isolated and wrapped in the polar portion of this molecule, acting as an inert carrier, so that at the time of its application, the active ingredient does not react or become "contaminated" by other radicals. The ratio of the molecular weight of the polar fraction of the polyoxyl 40 stearate to the active ingredient (sodium dyclophenac) regards t the molecular weight of the polarized fraction should be 5.68. In order to achieve the above, an infinite number of combinations were made of other components, one compound and preparation sequence thereof being found through different tests, which would allow the values of polarity, conductivity, pH, (REDOX potential) and isotonicity to consequently give a compound which is not described in the literature and which demonstrates that its balance was achieved by considering this as a carrier compound of the active ingredient exclusively for ophthalmological topical formulations.

Figure 2:
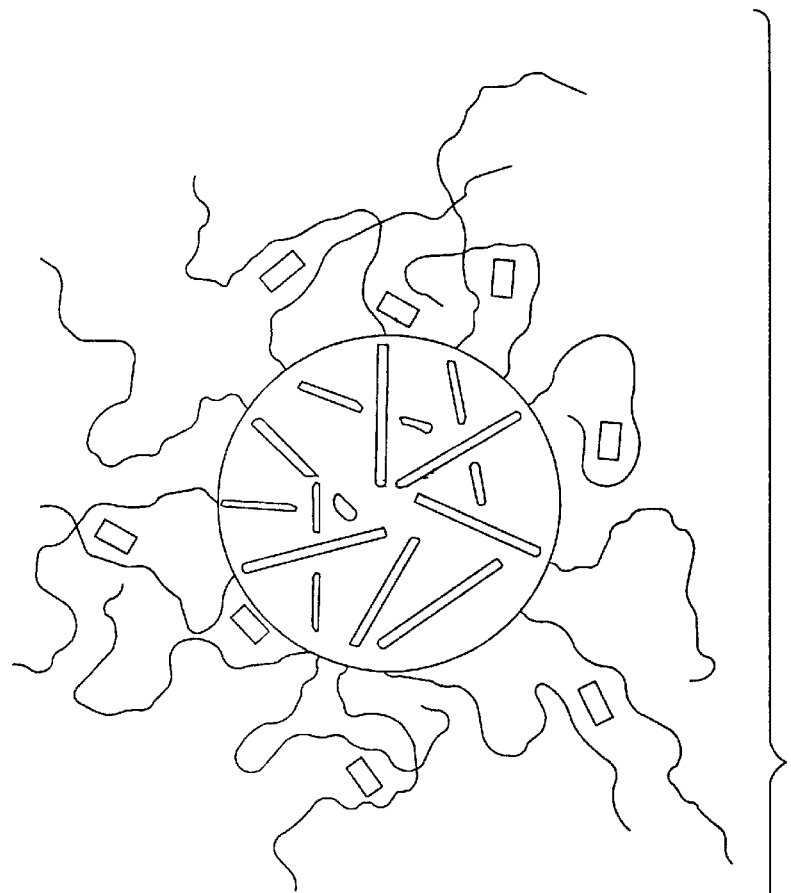
FIG. 2, is an illustration of a micella of polyoxyl stearate 40 linked to the main active ingredient (sodium dyclophenac) of this invention.
Figure 2:
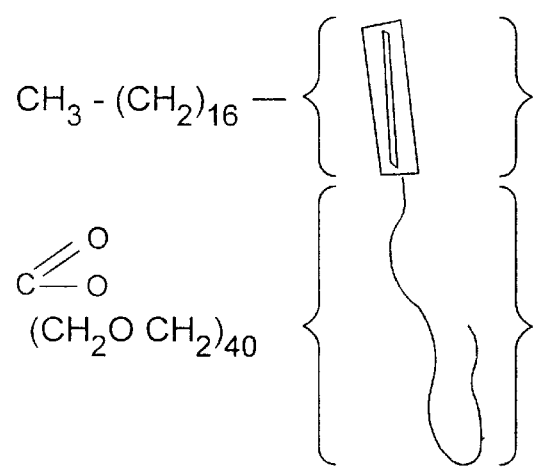

In FIG. 2, the polar part (2) of the polyoxyl stearate 40 can be seen, corresponding to the polyoxyethylene chain $(CH_2OCH_2)40$, linked to the molecules of the main active ingredient (3) (sodium dyclophenac). FIG. 1 is a diagram of the reaction which takes place between the components of the ophthalmic carrier compound and the main active ingredient.

The composition of the ophthalmic carrier solution of this invention is formed by the following ingredients:

OPHTHALMIC CARRIER SOLUTION

| INGREDIENT | AMOUNT | % BY WEIGHT |
|---|---|---|
| Polyoxyl stearate 40 | 7.0 g | 10.20 |
| Dehydrated disodium edetate | 0.1 g | 0.15 |
| Sodium Chloride | 0.7 g | 1.03 |
| Boric Acid | 0.095 g | 0.14 |
| Sorbic Acid | 0.22 g | 0.32 |
| Sodium Bisulfite | 0.040 g | 0.06 |
| Distilled water excipient | 100 ml | 88.00 |

The typical composition using the composition of the ophthalmic carrier solution shown in the above formula, also containing the active ingredient, in this case sodium dyclophenac, is as follows:

OPHTHALMIC COMPOSITION

| | | |
|---|---|---|
| Sodium dyclophenac | 0.1 | g |
| Polyoxyl stearate 40 | 7.0 | g |
| Dehydrated disodium edetate | 0.1 | g |
| Sodium Chloride | 0.7 | g |
| Boric Acid | 0.095 | g |
| Sorbic Acid | 0.22 | g |
| Sodium Bisulfite | 0.040 | g |
| Distilled water excipient | 100 | ml |

As has been described above, the polyoxyl stearate 40 has a formula and stoichiometry which allows the active ingredient to be isolated and wrapped in the polar portion of this molecule, acting as an inert carrier, so that at the time of its application, the active ingredient does not react or become "contaminated" by other radicals.

The dehydrated disodium edetate as a classic sequestering agent, is added to capture free ions which at a given moment could interfere with the isolating effect of the stearate.

NaCl is added in the amount shown in Table I to increase the isotonicity but principally the conductivity of the solution.

The boric acid is a pH regulating substance which is added with the aim of maintaining the pH value close to neutrality, so as to be compatible with human pre-corneal lachrymal film which has a pH of 7.0 to 7.4.

The sorbic acid is a preservative used in the preparation of ophthalmic solutions with the aim of protecting such solutions from any contamination by microorganisms. It is characterized by being a substance which does not irritate the eyeball and having a wide spectrum.

In this invention, sodium hydroxide is used to adjust the pH to neutrality protecting the oxide reduction potential of the already formed compound allowing the polar portion of the stearate to facilitate interaction with the main active ingredient when the latter is incorporated into the carrier solution.

The sodium methabisulfite has the characteristic of being highly antioxidant, making sure that none of the dissolved oxygen interacts with the main active ingredient and that the polar characteristic of the polyoxyl stearate 40 is not altered.

Before the main active ingredient solution is added to the carrier compound which allows the orientation of the polar groups of the polyoxyl stearate 40, ready for "capturing" the sodium dyclophenac, the carrier must have a pH of 6.98 and a conductivity of 16.97. The volume of the solution of the active ingredient (solution at 0.3%) must be 30% with regards to the volume of the stearate compound, constantly obtaining a reduction of 30% in the conductivity (dilution factor) and a final pH of 6.84.

Equipment Used in the Process

The following equipment is used in the preparation of the composition of this invention:

316 stainless steel tank, with a medical finish.

Medical type shaker with helix type 316 stainless steel propellers.

316 stainless steel tank, medical finish with an internal coil for the heating of distilled water.

Manufacturing Process

As an example of the preparation of the composition covered by this invention, the following sequence of steps and operating conditions was established:

1. Heat 60% of the distilled water of the total volume of the preparation to an approximate temperature of 69 to 71° C., making sure to adjust the pH to 6.245 (with a limit of ±0.25) and maintain a conductivity no greater than 0.002 mS/cm.
2. Empty the above described amount of distilled water into the stainless steel tank.
3. Place the shaker with its stainless steel propeller in the preparation tank.
4. Turn-on the shaker and select a speed of 800 rpm (±50 rpm).
5. Slowly add the polyoxyl stearate 40, maintaining the shaker at 800 rpm (with a limit of ±50 rpm), for a time of between 27 and 33 minutes; the pH at the end of the shaking time should be approximately between 6.0 and 6.2 and the conductivity after the shaking time should be 0.12 mS/cm (with a limit of ±0.05 mS/cm); in addition, the temperature after the shaking time should be between 63 and 67° C.
6. Add the disodium edetate to the $H_2O$ slowly, maintaining the shaker for a time of between 13 and 17 minutes at a speed of 750–850 rpm; the pH at the end of the shaking time should be within a range of 5.54 to 5.58 and the conductivity after the shaking time should be between 0.679 and 0.681 mS/cm; the temperature after the shaking time should be between 59 and 61° C.
7. Slowly add the sodium chloride, maintaining the shaker at a speed of between 750 and 850 rpm during an approximate time of 13 to 17 minutes; the pH at the end of the shaking time should be within a range of 5.20 to 5.22 and the conductivity after the shaking time should be between 15.32 and 17.32 mS/cm; the temperature after the shaking time should be between 55 and 57° C.
8. Slowly add the boric acid, maintaining the shaker at a speed of between 750 and 850 rpm during an approximate time of 13 to 17 minutes; the pH at the end of the shaking time should be within a range of 5.20 to 5.24 and the conductivity after the shaking time should be between 11.64 and 13.64 mS/cm; the temperature after the shaking time should be between 55 and 57° C.
9. Wait until the temperature of the preparation falls to approximately 49–51° C.
10. Slowly add the sorbic acid, maintaining the shaker at a speed of between 750 and 850 rpm during an approximate time of 13 to 17 minutes; the pH at the end of the shaking time should be within a range of 3.84 to 3.88 and the conductivity after the shaking time should be between 15.82 and 15.92 mS/cm; the temperature after the shaking time should be between 46 and 48° C.

11. Adjust the pH with sodium hydroxide as soon as possible to a value of 7.15±0.1, maintaining the shaker at a speed of between 750 and 850 rpm during an approximate time of 9 to 11 minutes; the conductivity after the shaking time should be between 16.06 and 18.06 mS/cm; the temperature after the shaking time should be between 44.5 and 45.5° C.

12. Wait until the temperature of the preparation falls to approximately 29–31° C.

13. Slowly add the sodium bisulfite, maintaining the shaker at a speed of between 750 and 850 rpm during an approximate time of 13 to 17 minutes; the pH at the end of the shaking time should be 7.0±0.1. The conductivity after the shaking time should be 16.97 mS/cm (with a limit of ±1.0 mS/cm); and the temperature after the shaking time should be between 25 and 29° C.

Preparation of the Active Ingredient Solution

14. Transfer 30% of the distilled water of the total volume of the preparation at an approximate temperature of 21 to 25° C. into a stainless steel container, position the shaker and select an approximate speed of between 580 and 620 rpm; add the sodium dyclophenac slowly, maintaining the shaker turned-on for approximately 13 to 17 minutes; the pH at the end of the shaking time should be 7.25±0.1. The conductivity after the shaking time should be 0.734 mS/cm (±1.0 mS/cm); and the temperature after the shaking time should be between 21 and 25° C.

15. Transfer the sodium dyclophenac preparation obtained in the previous step, into the tank which contains the rest of the ingredients, maintaining a shaker speed of 800±50 rpm for approximately 13 to 17 minutes.

16. Heat the total volume with distilled water to a temperature of 21 to 25° C. and with an approximate pH of between 6.00 and 6.50. The conductivity of the distilled water must not be greater than 0.002 mS/cm.

17. Shake the solution for a time of 2 hours ±5 minutes.

18. Adjust the pH at the end of the shaking time to a value between 6.83 and 6.85. The conductivity after the shaking time should be 11.77 mS/cm±0.5 mS/cm and the temperature after the shaking time should be approximately 21–25° C.

TABLE I

| Process stage | Conductivity mS/cm | Conductivity TDS g/L | Temperature °C. | pH |
|---|---|---|---|---|
| Distilled water | 0.002 | 0.001 | 70 | 6.25 |
| Polyoxyl stearate 40 | 0.12 | 0.0603 | 60 | 6.1 |
| Disodium edetate | 0.68 | 0.342 | 60 | 5.56 |
| Sodium chloride | 16.32 | 8.15 | 56 | 5.21 |
| Boric acid | 12.64 | 6.32 | 54 | 5.22 |
| Sorbic acid | 15.87 | 7.93 | 50 | 3.86 |
| Adjustment with NaOH | 17.06 | 8.52 | 35 | 7.21 |
| Sodium bisulfite | 16.97 | 8.47 | 30 | 6.98 |
| Mixture + dyclophenac | 11.77 | 5.88 | 22 | 6.84 |
| Dyclophenac alone | 0.734 | 0.368 | 22 | 7.25 |

EXAMPLES

Example 1
Preparation of the Ophthalmic Carrier Compound

As an example on an industrial scale of this invention, the following procedure was performed by which 200 lt of an ophthalmic carrier composition was prepared according to this invention:

120 lt of distilled water were heated to a temperature of 70° C., the pH was adjusted to 6.25, maintaining a conductivity no greater than 0.002 mS/cm. The hot distilled water was emptied into a stainless steel tank and shaken at an approximate speed of 800 rpm. While being shaken, 14.0 kg of polyoxyl stearate 40 were slowly added to the tanks and the shaking was continued for approximately 30 minutes, at the end of which the solution had a pH of 6.1, a conductivity of 0.12 mS/cm at a temperature of 65° C. Then 0.2 kg of sodium edetate were added, maintaining the shaking for approximately 15 minutes at a speed of 800 rpm. At the end of this stage the pH of the solution was 5.56 and the conductivity was 0.68 mS/cm at a temperature of 60° C. Next, 1.4 kg of sodium chloride were slowly added, maintaining the shaking at a speed of 800 rpm for 15 minutes, at the end of which, the pH of the solution was 5.21 and the conductivity was 16.32 mS/cm at a temperature of 56° C. Then, 0.19 kg of boric acid were slowly added, maintaining the shaking at a speed of 800 rpm for 15 minutes, at the end of which, the pH of the solution was 5.22 and the conductivity was 12.64 mS/cm at a temperature of 54° C. Next, the solution was left to cool to a temperature of 50° C. and 0.44 kg of sorbic acid were slowly added, maintaining the shaking at a speed of 800 rpm for 15 minutes, at the end of which, the pH of the solution was 3.86 and the conductivity was 15.87 mS/cm at a temperature of 47° C. The pH was immediately adjusted to 7.21 by the addition of sodium hydroxide, the solution being shaken at a speed of 800 rpm for 10 minutes. At this stage the conductivity was 17.06 mS/cm and the temperature of the solution was 45° C. The solution was left to cool to a temperature of 30° C. and then 0.080 kg of sodium bisulfite were slowly added, maintaining the shaking at a speed of 800 rpm for 15 minutes; a pH of 6.98, conductivity of 16.97 and a temperature of the solution of 30° C. were observed.

Example 2
Preparation of a Composition for Ophthalmic Use Containing the Carrier Compound and Sodium Dyclophenac as the Active Ingredient a) Preparation of the active ingredient solution:

60 liters of distilled water were emptied into a steel container, at a temperature of 23° C. and shaken at a speed of 600 rpm, 0.2 kg of sodium dyclophenac were slowly added, and shaken for 15 minutes. The pH of the solution at the end of the shaking was 7.25 and conductivity was 0.734 mS/cm, and the solution temperature of solution was 23° C.

b) Preparation of the ophthalmic composition containing the active ingredient:

The sodium dyclophenac solution was transferred into a stainless steel tank with a capacity of 200 liters, containing 120 liters of the carrier compound solution prepared in example 1. The solution was shaken at a speed of 8900 rpm for 15 minutes. The total volume of 200 liters with distilled water had a temperature of 23° C., a conductivity not greater than 0.002 mS/cm, and a pH of 6.25. The solution was shaken for approximately 2 hours and then the pH was adjusted to an approximate value of 6.84. The conductivity of the final solution was 11.77 and the final temperature of the solution was approximately 23° C.

It is hereby recorded that the best method known by the applicant for the practical use of the invention is that mentioned in the description and the examples, which are shown only as an illustration and in no way is intended to restrict the claimed invention.

Having described the invention above, the content of the following are claimed as property:

1. An ophthalmic carrier solution for use in the topical application of ophthalmic use compounds, said carrier solution comprising the following components:

10.20% by weight of polyoxyl stearate 40;

0.15% by weight of dehydrated disodium edetate;

1.03% by weight of sodium chloride;

0.14% by weight of boric acid;

0.32% by weight of sorbic acid;

0.06% by weight of sodium bisulfite, and 88.00% by weight of distilled water.

2. A process for preparing an ophthalmic carrier solution, said carrier solution comprising the following components: polyoxyl stearate 40, dehydrated disodium edetate, sodium chloride, boric acid, sorbic acid, sodium bisulfite and distilled water, said process comprising the following steps:

a) Heating a predetermined volume of distilled water to an approximate temperature of 69 to 71° C.; adjusting the pH to 6.25 (±0.25) and maintaining a conductivity no greater than 0.002 mS/cm;

b) Emptying the heated distilled water into a stainless steel tank;

c) Adding the polyoxyl stearate 40 slowly to the heated distilled water; maintaining the shaker operating for a time of between 27 and 33 minutes, the pH at the end of the shaking time being approximately between 6.0 and 6.2, the conductivity after the shaking time being 0.12 mS/cm (±0.05 mS/cm), and the temperature after the shaking time being between 63 and 67° C.;

d) Adding the disodium edetate to $H_2O$ slowly to the tank, maintaining the shaker operating for a time of between 13 and 17 minutes at a speed of 750–850 rpm, the pH at the end of the shaking time being within a range of 5.54 to 5.58, the conductivity after the shaking time being between 0.679 and 0.681 mS/cm, and the temperature after the shaking time being between 59 and 61° C.;

e) Adding the sodium chloride slowly to the tank, maintaining the shaker at a speed of between 750 and 850 rpm during an approximate time of 13 to 17 minutes; the pH at the end of the shaking time being within a range of 5.20 to 5.22, the conductivity after the shaking time being between 15.32 and 17.32 mS/cm, and the temperature after the shaking time being between 55 and 57° C.;

f) Adding the boric acid slowly to the tank, maintaining the shaker at a speed of between 750 and 850 rpm during an approximate time of 13 to 17 minutes; the pH at the end of the shaking time being within a range of 5.20 to 5.24, the conductivity after the shaking time being between 11.64 and 13.64 mS/cm, and the temperature after the shaking time being between 55 and 57° C.;

g) Cooling to approximately 49–51° C.;

h) Adding the sorbic acid slowly to the tank, maintaining the shaker at a speed of between 750 and 850 rpm during an approximate time of 13 to 17 minutes; the pH at the end of the shaking time being within a range of 3.84 to 3.88, the conductivity after the shaking time being between 15.82 and 15.92 mS/cm, and the temperature after the shaking time being between 46 and 48° C.;

i) Adjusting the pH with sodium hydroxide as soon as possible to a value of 7.15±0.1, maintaining the shaker at a speed of between 750 and 850 rpm during an approximate time of 9 to 11 minutes; the conductivity after the shaking time being between 16.06 and 18.06 mS/cm, and the temperature after the shaking time being between 44.5 and 45.5° C.;

j) Cooling to approximately 29–31° C.;

k) Adding the sodium bisulfite slowly to the tank, maintaining the shaker at a speed of between 750 and 850 rpm during an approximate time of 13 to 17 minutes; the pH at the end of the shaking time being 7.0±0.1, the conductivity after the shaking time being 16.97 mS/cm±1.0 mS/cm), and the temperature after the shaking time being between 25 and 29° C.

3. An ophthalmic composition for topical use, which comprises:

68.16% by weight of the carrier solution of claim 1;

0.10% by weight of an active agent which is an anti-inflammatory agent or an antibiotic; and distilled water to 100% by weight of the solution.

4. An ophthalmic composition for topical use according to claim 3, wherein said anti-inflammatory agent is sodium dyclophenac.

5. A process for preparing an ophthalmic composition for topical use which consists of an ophthalmic carrier solution according to claim 1 and an active ingredient which is sodium dyclophenac or an antibiotic which is tobramicin or gentamicin, said process consisting of the following steps:

i) emptying a predetermined amount of distilled water into a stainless steel container; shaking said container at an approximate speed of between 580 and 620 rpm; adding the sodium dyclophenac slowly, maintaining the shaker turned-on for approximately 13 to 17 minutes: the pH at the end of the shaking time being 7.25±0.1. The conductivity after the shaking time being 0.734 mS/cm (±1.0 mS/cm); and the temperature after the shaking time being between 21 and 25° C.;

ii) transferring the sodium dyclophenac solution obtained in the previous step, into a tank containing a predetermined volume of the carrier solution prepared according to the process of claim 2, maintaining a shaker speed of 800±50 rpm for approximately 13 to 17 minutes;

iii) heating the solution of (ii) with distilled water to a temperature of 21 to 25° C. and with an approximate pH of between 6.00 and 6.50, the conductivity of the distilled water being no greater than 0.002 mS/cm;

iv) shaking the solution for a time of 2 hours±5 minutes; and v) adjusting the pH at the end of the shaking time to a value between 6.83 and 6.85, the conductivity after the shaking time being 11.77 mS/cm±0.5 mS/cm and the temperature after the shaking time being approximately 21–25° C.

6. An ophthalmic carrier solution consisting essentially of the following components in aqueous solution:

10.20% by weight of polyoxyl stearate 40;

0.15% by weight of dehydrated disodium edetate;

1.03% by weight of sodium chloride;

0.14% by weight of boric acid;

0.32% by weight of sorbic acid; and 0.06% by weight of sodium bisulfite.

7. An ophthalmic composition for topical use consisting essentially of the carrier solution of claim 6 and an active ingredient in an amount sufficient to effect treatment of an eye.

8. A process for preparing an ophthalmic carrier solution according to claim 2, which consists essentially of the enumerated steps.

9. An ophthalmic composition according to claim 3, wherein the antibiotic is tobramicin, gentamicin or timolol sulfate.

* * * * *